United States Patent
Dean

(10) Patent No.: US 6,710,085 B2
(45) Date of Patent: Mar. 23, 2004

(54) METHODS FOR ENHANCING PLANT GROWTH USING DIACYL UREAS

(75) Inventor: Frank William Dean, Spring, TX (US)

(73) Assignee: Stoller Enterprises, Inc., Houston, TX (US)

(*) Notice: Subject to any disclaimer, the term of this patent is extended or adjusted under 35 U.S.C. 154(b) by 0 days.

(21) Appl. No.: 10/207,505

(22) Filed: Jul. 29, 2002

(65) Prior Publication Data

US 2003/0145640 A1 Aug. 7, 2003

Related U.S. Application Data

(62) Division of application No. 09/514,995, filed on Feb. 29, 2000, now Pat. No. 6,448,440, which is a division of application No. 08/831,799, filed on Apr. 9, 1997, now Pat. No. 6,040,273.

(60) Provisional application No. 60/015,130, filed on Apr. 10, 1996.

(51) Int. Cl.$^7$ ............................................. A01N 47/28
(52) U.S. Cl. ................. 514/594; 504/327; 47/57.6; 564/44; 564/45; 560/157; 560/158; 560/159
(58) Field of Search ................. 504/327; 514/594; 47/57.6; 564/44, 45; 560/157, 158, 159

(56) References Cited

U.S. PATENT DOCUMENTS

| | | | |
|---|---|---|---|
| 773,251 A | 11/1904 | Fischer et al. | 564/45 |
| 2,135,064 A | 11/1938 | Whitmore et al. | 564/45 |
| 4,935,413 A | 6/1990 | Urano et al. | 514/178 |
| 4,950,323 A | 8/1990 | Kezerian | 71/120 |

FOREIGN PATENT DOCUMENTS

| | | |
|---|---|---|
| DE | 90137 | 5/1972 |
| RU | 570579 | 10/1977 |

OTHER PUBLICATIONS

Jirman, et al., Collection Czechoslovak Chem. Commun., vol. 52, pp. 2474–2481 (1987).
Jirman, et al., Collection Czechoslovak Chem. Commun., vol. 57, pp. 1278–1281 (1992).

*Primary Examiner*—Shailendra Kumar
(74) *Attorney, Agent, or Firm*—Walter R. Brookhart; Shook, Hardy & Bacon, LLP

(57) ABSTRACT

The present invention is directed to new compositions of matter comprising the reaction products of a carboxylic acid and a urea having the formula:

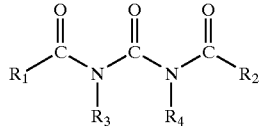

where $R_1$, $R_2$, $R_3$ and $R_4$ are the same or different and are selected from the group consisting of hydrogen, substituted and unsubstituted alkyl, allyl, vinyl and alkoxyl groups having from 1–6 carbon atoms, substituted and unsubstituted phenyl groups and the halides. Preferably, the reaction product of the present invention is N,N'-diformylurea or N,N'-diacetylurea. These reaction products, e.g., diformylurea, have been found to produce significantly improved growth in a variety of agricultural products when applied to the seed, to the surrounding soil or to the foliage of the emerging plant. Because of the similarity in the carbon, nitrogen, oxygen structure of these reaction products with many biological compounds, it is believed that the reaction products of the present invention may find use in a variety of biological applications.

20 Claims, No Drawings

METHODS FOR ENHANCING PLANT GROWTH USING DIACYL UREAS

This application is a division of U.S. patent application Ser. No. 09/514,995, filed Feb. 29, 2000, and issued on Sep. 20, 2002, as U.S. Pat. No. 6,448,440. The '440 patent is, in turn, a division of U.S. patent application Ser. No. 08/831,799, filed Apr. 9, 1997, and issued on Mar. 21, 2000, as U.S. Pat. No. 6,040,273. Further, this application claims priority of United States Provisional Patent Appln. No. 60/015,130, filed Apr. 10, 1996.

BACKGROUND OF THE INVENTION

1. Field of the Invention

The present invention generally relates to new substituted ureas, to methods for preparing those substituted ureas and to agricultural uses of those substituted ureas to improve plant growth. More specifically, the present invention is directed to the reaction product formed by reacting a carboxylic acid with urea to form a new N,N'-di-substituted urea, to methods for conducting that reaction and to agricultural uses of the reaction product.

2. Description of the Background

Urea, being approximately 46% by weight nitrogen, has long been preferred as a nitrogen source for fertilizing soils to stimulate plant growth. However, urea suffers from high ammonia losses when used in the presence of moisture. This disadvantage effectively restricted the use of urea for many years. It is believed that these losses are caused by the hydrolysis of urea in the presence of moisture and the enzyme urease. The addition of a water soluble salt to aqueous solutions of urea has been suggested as a means for reducing ammonia volatilization. See U.S. Pat. No. 4,500,335. While substituted ureas are also known, e.g., diphenylurea, they have found little agricultural use.

Urea undergoes condensation reactions with carboxylic acids to produce barbituates and their analogs. These products have found no agricultural uses. However, the agricutural industry has felt the need for ways to improve early seedling vigor and to increase plant biomass, both resulting in improved yield. There has been a long felt but unfulfilled need in the industry for improved methods for achieving these goals. The present invention solves those needs.

SUMMARY OF THE INVENTION

The present invention is directed to new compositions of matter comprising the reaction product of a carboxylic acid and a urea, including mono- and di-substitued ureas. The reaction product of the present invention comprises an N,N'-di-substituted urea having the formula:

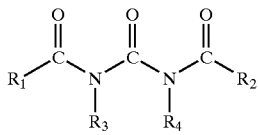

where $R_1$, $R_2$, $R_3$ and $R_4$ are the same or different and are selected from the group consisting of hydrogen, substituted and unsubstituted alkyl, allyl, vinyl and alkoxyl groups having from one to six carbon atoms, substituted and unsubstituted phenyl groups and the halides.

In a preferred embodiment, the second reactant is unsubstituted urea so that $R_3$ and $R_4$ in the reaction product are hydrogen. In a more preferred embodiment, $R_1$ and $R_2$ are selected from the group consisting of hydrogen and alkyl groups having from one to three carbon atoms. Most preferably, formic acid is reacted with urea in a molar ratio of about 2:1 to produce N,N'-diformylurea. While the reaction may be conducted at any temperature between about 10° C. and about 140° C., it is preferably conducted within the range of about 15° C. to about 40° C. The reaction may conveniently be conducted at room temperature. Preferably the reactants are stirred until the reaction mixture is clear. Crystals of the reaction product will form and may be separated from the reaction mixture.

The reaction products of the present invention, most preferably N,N'-diformylurea has been found to produce enhanced growth in plants when used in a variety of ways. These reaction products, most preferably diformylurea, produce enhanced growth when applied to seeds prior to planting, when applied to the soil surrounding the plant at or after planting or when applied to the foliage of the plant, e.g., at the three leaf stage of growth. An aqueous solution containing from about 0.001–1.0 M of the reaction product may be applied to the surface of seeds at a rate of about 15–750 ml. of solution per 100 lbs of seed. In a convenient method, the solution may be applied to the surface of the seeds or the seeds may be soaked in such a solution for about 2–24 hours, preferably for about 24 hours, prior to planting. Alternatively, such a solution may be applied to the soil surrounding the seed and/or emerging plant. When so applied, it is suggested that the solution be applied at a rate of about 1–100 grams of diformylurea or other reaction product per acre. Still another alternative is the application of such an aqueous solution to the foliage of the plant, preferably at the three leaf growth stage, at a rate of about 1–100 grams of diformylurea or other reaction product per acre. When applied to the foliage, those skilled in the art may include a conventional vegetable oil and surfactant in the solution to improve the retention of reaction product on the leaves so that it may be more readily absorbed by the plant.

The newly discovered reaction products of urea and carboxylic acids described herein, particularly N,N'-diformylurea, have produced significantly improved growth when applied to the seeds and foliage of a variety of agricultural products. Accordingly, it is believed that a significant improvement in crop development may be obtained using these new products. These and other meritorious features and advantages of the present invention will be more fully appreciated from the following detailed description and claims.

DETAILED DESCRIPTION OF THE PREFERRED EMBODIMENT

The present invention provides methods for preparing and using the reaction products of a carboxylic acid and a urea comprising new compositions of matter. It has been found that these reaction products may be easily prepared and that they may have significant agricultural uses because of their perceived biological activity. In fact, it has been found that these reaction products, specifically N,N'-diformylurea, enhance the growth of a variety of agricultural crops when applied to the seeds, surrounding soil or foliage.

The reaction products of the present invention have the general formula:

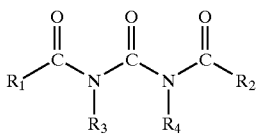

where $R_1$, $R_2$, $R_3$ and $R_4$ are the same or different and are selected from the group consisting of hydrogen, substituted and unsubstituted alkyl, allyl, vinyl and alkoxyl groups having from 1–6 carbon atoms, substituted and unsubstituted phenyl groups and the halides. These reaction products are prepared by reacting a carboxylic acid having the formula RCOOH where R is selected from the group consisting of hydrogen, substituted and unsubstituted alkyl, allyl, vinyl and alkoxyl groups having from 1–6 carbon atoms, substituted and unsubstituted phenyl groups and the halides. Exemplary acids include formic acid, acetic acid, propionic acid, butyric acid, valeric acid, caproic acid, heptanoic acid, and citric acid. Preferably R is selected from the group consisting of hydrogen and unsubstituted alkyl groups having from 1–3 carbon atoms. The presently most preferred acids are formic or acetic acid. These carboxylic acids are reacted with a substituted or unsubstituted urea having the formula $(NHR')_2CO$ where each R' is the same or different and is selected from the group consisting of hydrogen, substituted and unsubstituted alkyl groups having from 1–6 carbon atoms, substituted and unsubstituted alkoxyl groups having from 1–6 carbon atoms, substituted and unsubstituted phenyl groups and the halides. Unsubstituted urea is the presently most preferred reactant.

In its most preferred embodiment, the present invention comprises the reaction product of urea and formic acid, i.e., N,N'-diformylurea, having the following formula:

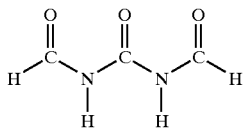

It has been found that the reaction of the present invention will proceed throughout a wide range of temperatures, e.g., from about 10° C. to about 140° C., restricted only by the boiling points of the reactants and products. While heat may be added by any conventional means to speed the rate of these reactions, it has been found that the methods of the present invention may conveniently be performed in a temperature range from about 15° C. to about 40° C., preferably at room temperature, i.e., from about 20° C. to about 30° C. These reactions appear to be slightly exothermic. The reaction of formic acid and urea to form diformylurea proceeds to completion within 24 hours at room temperature. It is preferred that the reaction mixture be stirred until clear and then permitted to remain quiescent until crystals of the reaction product have formed.

It is believed that the reactions proceed by the elimination of two water molecules. The reaction of urea and formic acid proceeds as follows:

$$H_2NCONH_2 + 2RCOOH \rightarrow RCONHCONHCOR + 2H_2O$$

In this reaction, formic acid reacts with one hydrogen on each of the urea nitrogens to produce N,N'-diformylurea. Accordingly, it is preferred that the reaction mixture comprise about 2 moles of carboxylic acid for each mole of urea.

Applicant believes that these reaction products will be biologically active as a result of the similarity of their skeletal structure, i.e., the nitrogen-carbon-oxygen skeleton, with the alternating double bond structure of these same elements in a variety of synthetic and naturally occurring biological molecules. Thus, it is believed that these reaction products, e.g., N,N'-diformylurea, will find a variety of biological uses. Applicant believes that these compounds may be used to produce, not only the improved plant growth shown herein, but that with the substitution of appropriate functional groups or bulky substituents, a variety of effective algaecides, herbicides, fungicides or pesticides may be produced.

Applicant believes that the reaction products claimed herein, particularly N,N'-diformylureas, may mimic plant growth hormones and/or plant growth regulators based upon the similarity of their skeletal structure to a variety of biologically active compounds. Common to all biologically active molecules in this class is a core structure including both alternating double bonds and alternating carbon to nitrogen bonds. These structures are common in all synthetically produced and naturally occurring biologically active molecules, e.g., cytokinens, substituted uracils, methylguanine and the like. While adenine and guanine have a fused ring structure, cytosine, thymine and uracil exhibit the same structures as pyrimidines. Because the N,N'-di-substituted ureas of the present invention, e.g., diformylurea, are linear, they can conform to the shapes of these biological molecules. While this conformation is not exact, it is believed that this feature will facilitate the biological activity of these molecules.

The reaction products of the present invention, specifically N,N'-diformylurea, have been used to enhance the growth of plants. In fact, it has been found that improved growth may be obtained by applying diformylurea to the seeds, or to the soil surrounding the plant, or to the foliage of the plant. A single application of diformylurea has been found to produce significantly greater growth in a variety of crops, including wheat, corn, peanuts, soybeans, rice and cotton. For example, a single application to rice at the rate of 50 grams per acre at tillering has produced a 25 percent increase in yield.

In one method of the present invention, seeds are treated with an aqueous solution containing the N,N'-di-substituted reaction product of a carboxylic acid and urea. Seeds may conveniently be soaked in an aqueous solution of the reaction product for a time from about 2–24 hours. Excellent results have been obtained with seeds soaked in an aqueous solution of diformylurea for about 24 hours. The seeds may be immediately planted or may be dried to produce a seed which has been treated with the reaction product.

While those skilled in the art will be able to prepare aqueous solutions of the desired concentration for these agricultural uses, it has been found that solutions containing from about 0.001–1.0 M of the reaction product are typically appropriate. Aqueous solutions containing from about 0.001–0.050 M are presently preferred. While these solutions may be applied at any rate desired by those of skill in the art, it has been found that aqueous solutions of the foregoing concentration provide good results when applied at the rate of about 15–750 ml. per 100 lbs of seed. Alternatively, it is believed that the reaction products of the present invention, typically in aqueous solutions of the foregoing concentrations, may be added to the soil surrounding the seed at planting or after emergence of the plant.

In another alternative method, excellent results have been obtained by a one time spraying of the foliage of the emerging plant, preferably at the three leaf stage, with an aqueous solution containing the reaction product. Those skilled in the art would be aware that addition of a small quantity of oil and/or surfactant to the aqueous solution sprayed on the foliage will improve the adherence of the reaction product to the leaves and the uptake of the reaction product by the plant. Suitable oils include both saturated and unsaturated oils, alcohols, esters and other compounds having both hydrosphobic and hydrophilic functional groups. Exemplary oils comprise the vegetable oils and include sunflower oil and soybean oil. Exemplary biologically acceptable surfactants include the organic polyphosphates and ethoxylated nonophenols. Again, those skilled in the art can determine appropriate concentrations for each desired use. However, aqueous solutions having the foregoing concentrations are believed to be generally appropriate. These solutions should be applied at a rate sufficient to provide about 1–100 grams of reaction product per acre.

The following are examples illustrating methods for preparing reaction products of the present invention, specifically N,N'-diformylurea and N,N'-diacetylurea, and results of applying diformylurea to a variety of agricultural crops.

The Preparation of N,N'-Diformylurea

Diformylurea has been prepared by reacting formic acid with urea in a molar ratio of about 1.8–2.0 moles formic acid to 1.0 mole urea. In a first example, 600 grams of urea was reacted with 920 grams of 90% formic acid. The molar ratio of formic acid to urea in this example is about 1.8 to 1. In a second example, 555 grams of urea was reacted with 945 grams of 90% formic acid. In this example, the molar ratio of formic acid to urea is about 2:1. The reaction mixture of both examples was stirred about 1 hour until the solution was clear. The clear solution was allowed to stand for about 48 hours at room temperature. Within 24 hours, substantially all of the reaction mixture had crystalized. At about 48 hours, the remaining liquid was decanted and the crystals purified by rinsing with the mother liquor and ice water using vacuum filtration. Upon analysis, only a single reaction product, i.e., N,N'-diformylurea, was found. Unexpectedly the formic acid had reacted on both of the urea nitrogens.

Preparation of N,N'-Diacetylurea

Diacetylurea was prepared by reacting 219 grams of urea with 438 grams of 99% acetic acid. The molar ratio of acetic acid to urea is about 2:1. The reaction mixture was stirred for about 1 hour until clear as before. Upon standing, crystals of N,N'-diacetylurea formed. The crystals were purified as described above.

It is believed that the reaction of carboxylic acid and urea may be accelerated by addition of a catalytic quantity of a transition metal, e.g., iron or zinc oxide or a complex of copper II and the reaction product of formic acid and urea described above.

Agricultural Use of N,N'-Diformylurea

In a preliminary experiment to determine the agricultural value of the N,N'-diformylurea prepared above, a concentrate was prepared by mixing 200 grams diformylurea and 200 grams formic acid, adjusting the ph to about 5.5 by the addition of potassium hydroxide and adding sufficient water to make 1 liter. This results in a concentrate having a concentration of 1.7 M diformylurea and 4.3 M formate. Low, medium and high dilution aqueous solutions were prepared by diluting, respectively, 0.8 grams, 8.0 grams and 40.0 grams of the concentrate per liter of final solution. Thus, the concentration of diformylurea in the low dilution was 0.0013 M. The concentration of diformylurea in the medium dilution was 0.013 M., while the high concentration dilution had a concentration of 0.068 M. diformylurea.

The foregoing solutions were used to coat corn, soybean, cotton and rice seeds prior to planting. Coating was achieved by soaking the seeds in the foregoing solutions for about 24 hours. Sufficient solution was used to keep the seeds immersed. Control seeds were soaked in water for the same time.

Untreated or control seeds, together with seeds treated by the low, medium and high dilution solutions, were planted in 1 gallon greenhouse pots. Six pots were used for each dilution or control with five seeds planted per pot. The plants were thinned to two plants per pot after emergence. The plants were watered and fertilized as required. After 30 days the plants were harvested and the roots and shoots examined.

The roots and shoots were weighed separately and the root/shoot ratio determined. The treated plants were generally characterized by both greater root mass and shoot mass when compared to the controls. The root/shoot ratio for most of the treated plants was greater than that for the controls. Further, the older leaves of plants grown from the treated seeds appeared to exhibit greater length and width than those from plants grown from the untreated seeds. Finally, crown roots were noticed on both corn and rice plants grown from the treated seeds. The results of these preliminary tests are summarized in Table I.

TABLE I

|  | Seed Treated | | | |
|---|---|---|---|---|
|  | Control | Low | Medium | High |
| Cotton | | | | |
| Roots (gm) | 3.03 | 7.85 | 4.50 | 5.07 |
| Shoots (gm) | 4.57 | 5.38 | 5.25 | 6.90 |
| Total (gm) | 7.60 | 13.23 | 9.75 | 11.97 |
| Root/Shoot Ratio | 0.66 | 1.46 | 1.08 | 0.73 |
| Rice | | | | |
| Roots (gm) | 0.47 | 0.61 | 3.07 | 0.82 |
| Shoots (gm) | 0.24 | 0.34 | 1.84 | 0.39 |
| Total (gm) | 0.71 | 0.95 | 4.91 | 1.21 |
| Root/Shoot Ratio | 1.95 | 1.78 | 1.86 | 2.10 |
| Corn | | | | |
| Roots (gm) | 9.00 | 9.80 | 10.40 | 9.60 |
| Shoots (gm) | 9.60 | 9.40 | 9.60 | 8.80 |
| Total (gm) | 18.60 | 19.20 | 20.00 | 18.40 |
| Root/Shoot Ratio | 0.94 | 1.04 | 1.08 | 1.09 |
| Soybean | | | | |
| Roots (gm) | 2.40 | 4.60 | 4.90 | — |
| Shoots (gm) | 3.80 | 4.90 | 4.10 | — |
| Total (gm) | 6.20 | 9.50 | 9.00 | — |
| Root/Shoot Ratio | 0.63 | 0.93 | 1.20 | — |

Table I illustrates the improved growth achieved by treating seeds prior to planting with an aqueous solution containing diformylurea. In substantially every example the treated seeds produced plants having greater root mass, greater shoot mass and greater total mass. Further, the ratio of root to shoot mass was increased in all of the treated cotton, corn and soybean samples.

Based upon the foregoing preliminary work, additional experiments to investigate the effect of diformylurea on other plant species was undertaken. These experiments were also designed to compare the effect of treating seeds as described above with foliar treatment. Wheat, corn and peanuts were selected for the next phase of this work. Diformylurea was prepared by reacting formic acid and urea at a molar ratio of 2:1 as described above. An aqueous solution containing diformylurea at a concentration of 0.01

M was prepared. For the seed treatment portion of the experiments, the seeds to be treated were soaked in the foregoing solution for about 24 hours before planting. The control seeds were again soaked in water for the same time. Both control and treated seeds were planted in 1 gallon greenhouse pots. Five seeds were planted in each pot. Each pot was thinned to two plants after germination. For the foliar treatment portion of the experiment, plants grown from untreated seeds were sprayed with a solution containing 0.01 M. diformylurea at the three leaf stage. All plants were watered and fertilized as required. Thirty days after planting, the plants were harvested and the roots and shoots examined. The mass of both the roots and shoots and the total mass of the plant in each pot were determined. The results for these experiments for control, seed treated and foliar treated wheat, corn and peanuts are reported in Tables II–IV, respectively.

A review of Tables II–IV establishes that the root mass, shoot mass and total plant mass appear to be increased in response to both treatment of the seeds and foliar treatment of the emerging leaves with an aqueous solution of diformylurea for each of the three tested crops. Average weights for the plants grown from untreated, seed treated and foliar treated seeds for each crop are reported in Table V.

TABLE II

Wheat

| | Control | | | Seed Treated 0.01 M diformylurea | | | Foliar Treated 0.01 M diformylurea | | |
|---|---|---|---|---|---|---|---|---|---|
| Sample | Roots (gm) | Shoots (gm) | Total (gm) | Roots (gm) | Shoots (gm) | Total (gm) | Roots (gm) | Shoots (gm) | Total (gm) |
| 1 | 12.10 | 1.41 | 13.51 | 46.50 | 9.76 | 56.26 | 14.00 | 4.00 | 18.00 |
| 2 | 30.04 | 3.19 | 33.23 | 65.06 | 12.94 | 78.00 | 26.81 | 7.28 | 34.09 |
| 3 | 29.63 | 5.15 | 34.78 | 27.98 | 4.17 | 32.15 | 37.26 | 7.48 | 44.74 |
| 4 | 14.98 | 2.03 | 17.01 | 41.69 | 12.22 | 53.91 | 25.13 | 7.53 | 32.66 |
| 5 | | | | 59.01 | 15.66 | 74.67 | 20.12 | 4.44 | 24.56 |
| 6 | 17.90 | 2.36 | 20.26 | 32.14 | 7.32 | 39.46 | 20.28 | 4.62 | 24.90 |
| average | 20.93 | 2.83 | 23.76 | 45.40 | 10.35 | 55.74 | 23.93 | 5.89 | 29.83 |

TABLE III

Corn

| | Control | | | Seed Treated 0.01 M diformylurea | | | Foliar Treated 0.01 M diformylurea | | |
|---|---|---|---|---|---|---|---|---|---|
| Sample | Roots (gm) | Shoots (gm) | Total (gm) | Roots (gm) | Shoots (gm) | Total (gm) | Roots (gm) | Shoots (gm) | Total (gm) |
| 1 | 55.31 | 43.19 | 98.50 | 57.78 | 46.12 | 103.90 | 42.18 | 67.57 | 109.75 |
| 2 | 50.53 | 26.16 | 76.69 | 80.82 | 34.73 | 115.55 | 66.57 | 56.61 | 123.18 |
| 3 | 50.91 | 24.55 | 75.46 | 38.15 | 17.33 | 55.48 | 42.40 | 61.80 | 104.20 |
| 4 | 30.95 | 29.65 | 60.60 | 57.78 | 46.12 | 103.90 | 48.44 | 46.17 | 84.61 |
| 5 | 39.73 | 17.53 | 57.26 | 80.82 | 34.73 | 115.55 | 52.48 | 50.59 | 103.07 |
| 6 | 45.49 | 28.22 | 73.71 | 38.15 | 17.33 | 55.48 | 56.22 | 61.12 | 117.34 |
| average | 46.15 | 28.22 | 74.37 | 58.92 | 32.73 | 91.65 | 51.38 | 57.31 | 108.69 |

TABLE IV

Peanuts

| | Control | | | Seed Treated 0.01 M diformylurea | | | Foliar Treated 0.01 M diformylurea | | |
|---|---|---|---|---|---|---|---|---|---|
| Sample | Roots (gm) | Shoots (gm) | Total (gm) | Roots (gm) | Shoots (gm) | Total (gm) | Roots (gm) | Shoots (gm) | Total (gm) |
| 1 | 18.46 | 14.66 | 33.12 | 16.46 | 20.20 | 36.66 | 31.69 | 36.17 | 67.86 |
| 2 | 17.29 | 10.86 | 28.15 | 22.65 | 22.00 | 44.65 | 33.55 | 31.82 | 65.37 |
| 3 | 15.96 | 10.60 | 26.56 | 20.11 | 20.46 | 40.57 | 27.67 | 28.38 | 56.05 |
| 4 | 13.19 | 14.77 | 27.96 | 22.04 | 22.34 | 44.38 | 35.04 | 30.34 | 65.38 |
| 5 | 19.52 | 17.85 | 37.37 | 21.60 | 19.03 | 40.63 | 37.38 | 33.84 | 71.22 |
| 6 | 17.92 | 23.90 | 41.82 | 16.74 | 17.77 | 34.51 | 31.10 | 32.35 | 63.45 |
| average | 17.06 | 15.44 | 32.50 | 19.93 | 20.30 | 40.23 | 32.74 | 32.15 | 64.89 |

TABLE V

| | | Wheat | | | Corn | | | Peanuts | | |
|---|---|---|---|---|---|---|---|---|---|---|
| | | Control | Seed Treated | Foliar Treated | Control | Seed Treated | Foliar Treated | Control | Seed Treated | Foliar Treated |
| | Roots (gm) | 20.93 | 45.40 | 23.93 | 46.15 | 58.92 | 51.38 | 17.06 | 19.93 | 32.74 |
| | Shoots (gm) | 2.83 | 10.35 | 5.89 | 28.22 | 32.73 | 57.31 | 15.44 | 20.30 | 32.15 |
| | Total (gm) | 23.76 | 55.74 | 29.83 | 74.37 | 91.65 | 108.69 | 32.50 | 40.23 | 64.89 |
| | Root/Shoot Ratio | 7.40 | 4.39 | 4.06 | 1.61 | 1.80 | 0.90 | 1.10 | 0.98 | 1.02 |
| Percent | Roots | | 117 | 14 | | 30 | 11 | | 17 | 92 |
| Change v. | Shoots | | 266 | 108 | | 16 | 103 | | 31 | 108 |
| Control | Total | | 135 | 26 | | 24 | 46 | | 24 | 100 |

The observed average weights for the roots, shoots and total mass, together with the percentage change versus control, for each of the three crops for both seed and foliar treatment are listed in Table V. Root mass, shoot mass and total mass increased for each of these three crops when treated with diformylurea, whether seed or foliar applied. The mass of the seed treated wheat was 135% greater than the control while that of the foliar treated peanuts was 100% greater. The remaining total mass results showed increases of 24–46% with respect to the control. The root to shoot ratios in these experiments were mixed. It appears that increased plant mass, both root and shoot, will be achieved by application of diformylurea to the seeds prior to planting or to the foliage after emergence.

Additional experiments were designed to study further the effect of the concentration of diformylurea applied to the seeds of several other crops. These experiments were conducted using cotton, rice, corn and soybeans. These experiments were similar to the preliminary experiments described above. The concentrate described above, containing both diformylurea and formate, was used to prepare solutions containing low, medium and high concentrations of diformylurea having, respectively, 0.001 M, 0.01 M and 0.05 M diformylurea. These solutions were used to treat the seeds of cotton, rice, corn and soybeans. Seeds of each of these crops were soaked in water or the prepared aqueous solutions of diformylurea for 24 hours before planting. Five seeds were planted in each of six, 1 gallon greenhouse pots. Pots were thinned to two plants after germination and the plants watered and fertilized as needed for 30 days. Thereafter, the plants were harvested and the mass of the roots, shoots and total mass determined. Those results, together with the averages are reported in Tables VI–IX.

TABLE VI

Cotton

| | Control | | | Seed Treated 0.001 M diformylurea | | | Seed Treated 0.01 M diformylurea | | | Seed Treated 0.05 M diformylurea | | |
|---|---|---|---|---|---|---|---|---|---|---|---|---|
| Sample | Roots (gm) | Shoots (gm) | Total (gm) | Roots (gm) | Shoots (gm) | Total (gm) | Roots (gm) | Shoots (gm) | Total (gm) | Roots (gm) | Shoots (gm) | Total (gm) |
| 1 | 4.70 | 4.80 | 9.50 | 6.90 | 5.70 | 12.60 | 6.90 | 4.80 | 11.70 | 4.70 | 6.90 | 11.60 |
| 2 | 1.50 | 4.50 | 6.00 | 9.20 | 5.70 | 14.90 | 2.40 | 4.60 | 7.00 | 6.60 | 7.00 | 13.60 |
| 3 | 2.90 | 4.40 | 7.30 | 3.80 | 4.80 | 8.60 | 1.90 | 4.00 | 5.90 | 4.30 | 4.70 | 9.00 |
| 4 | | | | 8.00 | 4.40 | 12.40 | 4.20 | 6.00 | 10.20 | 6.00 | 5.00 | 11.00 |
| 5 | | | | 10.00 | 6.20 | 16.20 | 7.60 | 4.90 | 12.50 | 4.20 | 6.40 | 10.60 |
| 6 | | | | 9.20 | 5.50 | 14.70 | 4.00 | 7.20 | 11.20 | 4.60 | 5.40 | 10.80 |
| Average | 3.03 | 4.57 | 7.60 | 7.85 | 5.38 | 13.23 | 4.50 | 5.25 | 9.75 | 5.07 | 5.90 | 10.97 |

TABLE VII

Rice

| | Control | | | Seed Treated 0.001 M diformylurea | | | Seed Treated 0.01 M diformylurea | | | Seed Treated 0.05 M diformylurea | | |
|---|---|---|---|---|---|---|---|---|---|---|---|---|
| Sample | Roots (gm) | Shoots (gm) | Total (gm) | Roots (gm) | Shoots (gm) | Total (gm) | Roots (gm) | Shoots (gm) | Total (gm) | Roots (gm) | Shoots (gm) | Total (gm) |
| 1 | 0.58 | 0.26 | 0.85 | 0.93 | 0.46 | 1.39 | 0.40 | 0.23 | 0.63 | 0.38 | 0.30 | 0.68 |
| 2 | 0.34 | 0.17 | 0.51 | 0.59 | 0.34 | 0.93 | 0.78 | 0.40 | 1.18 | 0.94 | 0.33 | 1.27 |
| 3 | 0.42 | 0.29 | 0.71 | 0.20 | 0.13 | 0.33 | 0.52 | 0.26 | 0.78 | 1.19 | 0.46 | 1.65 |
| 4 | | | | 0.55 | 0.37 | 0.92 | 0.27 | 0.13 | 0.40 | 0.21 | 0.18 | 0.39 |
| 5 | | | | 1.11 | 0.52 | 1.62 | 0.45 | 0.38 | 0.83 | 0.78 | 0.41 | 1.19 |
| 6 | | | | 0.28 | 0.23 | 0.51 | 0.65 | 0.44 | 1.09 | 1.43 | 0.63 | 2.06 |
| Average | 0.45 | 0.24 | 0.69 | 0.61 | 0.34 | 0.95 | 0.51 | 0.31 | 0.82 | 0.82 | 0.39 | 1.21 |

TABLE VII

| | Corn | | | | | | | | | | | |
|---|---|---|---|---|---|---|---|---|---|---|---|---|
| | Control | | | Seed Treated 0.001 M diformylurea | | | Seed Treated 0.01 M diformylurea | | | Seed Treated 0.05 M diformylurea | | |
| Sample | Roots (gm) | Shoots (gm) | Total (gm) | Roots (gm) | Shoots (gm) | Total (gm) | Roots (gm) | Shoots (gm) | Total (gm) | Roots (gm) | Shoots (gm) | Total (gm) |
| 1 | 20.50 | 18.80 | 39.30 | 18.10 | 18.90 | 37.00 | 15.30 | 15.50 | 30.80 | 21.20 | 18.40 | 39.60 |
| 2 | 18.30 | 17.90 | 36.20 | 17.60 | 19.50 | 37.10 | 24.80 | 19.70 | 44.50 | 18.70 | 15.80 | 34.50 |
| 3 | 19.00 | 17.10 | 36.10 | 18.90 | 21.10 | 40.00 | 16.20 | 18.60 | 34.80 | 17.90 | 17.40 | 35.30 |
| 4 | | | | 17.20 | 14.00 | 31.20 | 25.10 | 22.10 | 47.20 | 20.40 | 20.60 | 41.00 |
| 5 | | | | 27.00 | 17.60 | 44.60 | 24.10 | 23.00 | 47.10 | 17.80 | 15.90 | 33.70 |
| 6 | | | | 19.10 | 22.00 | 41.10 | 20.00 | 16.60 | 36.60 | | | |
| Average | 19.27 | 17.93 | 37.20 | 19.65 | 18.85 | 38.50 | 20.92 | 19.17 | 40.09 | 19.20 | 17.62 | 36.82 |

TABLE IX

| | Soybean | | | | | | | | |
|---|---|---|---|---|---|---|---|---|---|
| | Control | | | Seed Treated 0.01 M diformylurea | | | Seed Treated 0.01 M diformylurea | | |
| | Roots (gm) | Shoots (gm) | Total (gm) | Roots (gm) | Shoots (gm) | Total (gm) | Roots (gm) | Shoots (gm) | Total (gm) |
| 1 | 5.10 | 7.90 | 13.00 | 7.80 | 8.70 | 16.50 | 12.40 | 9.90 | 22.30 |
| 2 | 4.50 | 6.90 | 11.40 | 8.40 | 9.80 | 18.20 | 5.70 | 8.90 | 14.60 |
| 3 | 5.00 | 8.10 | 13.10 | 7.30 | 10.20 | 17.50 | 8.40 | 11.20 | 19.60 |
| 4 | | | | 8.00 | 10.30 | 18.30 | 5.00 | 6.00 | 11.00 |
| 5 | | | | 11.30 | 9.30 | 20.60 | 5.90 | 8.30 | 14.20 |
| 6 | | | | 12.30 | 10.90 | 23.20 | | | |
| Average | 4.87 | 7.63 | 12.50 | 9.18 | 9.87 | 19.05 | 7.48 | 8.86 | 16.34 |

Review of the data reported in the foregoing tables illustrates that cotton, rice, corn and soybean seeds treated with an aqueous solution of diformylurea consistently produced plants having increased root, shoot and total plant mass. These improved results were obtained over a wide concentration range from at least about 0.001M diformylurea to at least about 0.05 M diformylurea in the aqueous solution in which the seeds were soaked. Table X illustrates the percentage change with respect to control for the root, shoot and total plant mass in these experiments.

TABLE X

| | Root/Shoot Ratio | Percent Change v. Control | | |
|---|---|---|---|---|
| | | Roots | Shoots | Total |
| Cotton | | | | |
| Control | 0.66 | — | — | — |
| 0.001 M diformylurea | 1.46 | 159 | 18 | 74 |
| 0.01 M diformylurea | 0.86 | 49 | 15 | 28 |
| 0.05 M diformylurea | 0.86 | 67 | 29 | 44 |
| Rice | | | | |
| Control | 1.86 | — | — | — |
| 0.001 M diformylurea | 1.79 | 37 | 42 | 39 |
| 0.01 M diformylurea | 1.67 | 13 | 29 | 19 |
| 0.05 M diformylurea | 2.13 | 82 | 63 | 76 |
| Corn | | | | |
| Control | 1.07 | — | — | — |
| 0.001 M diformylurea | 1.04 | 2 | 5 | 3 |
| 0.01 M diformylurea | 1.09 | 9 | 7 | 8 |
| 0.05 M diformylurea | 1.09 | 0 | −2 | −1 |
| Soybean | | | | |
| Control | 0.64 | — | — | — |
| 0.001 M diformylurea | 0.93 | 89 | 29 | 52 |
| 0.01 M diformylurea | 0.84 | 54 | 16 | 31 |

In substantially every case, both root and shoot mass increased for plants emerging from seeds treated with diformylurea. The root to shoot ratio for these plants is also illustrated in Table X. The ratio increased for both cotton and soybean and remained generally the same for rice and corn.

The foregoing description of the invention has been directed in primary part to particularly preferred embodiments in accord with the requirements of the Patent Statute and for purposes of explanation and illustration. It will be apparent, however, to those skilled in the art that many modifications and changes in the specifically described system may be made without departing from the true scope and spirit of the invention. For example, while most of the work reported herein employs diformylurea, other N,N'-disubstituted ureas comprising the reaction product of carboxylic acids and urea may also be found to provide improved results. Further, those skilled in the art will be aware that the concentration of reaction product in aqueous solution may be adjusted as required based upon the nature of each crop or the application equipment. Therefore, the invention is not restricted to the preferred embodiments described and illustrated but covers all modifications which may fall within the scope of the following claims.

What is claimed is:

1. A method for enhancing the growth of a plant, comprising applying to seeds for said plant prior to planting, to soil surrounding said plant, or to foliage of said plant, an N,N'-substituted urea having the formula:

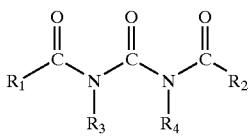

where $R_1$, $R_2$, $R_3$ and $R_4$ are the same, but not all hydrogen, or different and are selected from the group consisting of hydrogen, substituted and unsubstituted alkyl, allyl, vinyl and alkoxyl groups having from 1 to 6 carbon atoms, substituted and unsubstituted phenyl groups and the halides.

2. The method of claim 1 wherein an aqueous solution having a concentration from about 0.001–1.0 M of said N,N'-substituted urea is applied to said seeds at a rate of about 15–750 ml. of solution per 100 lbs. of seed.

3. The method of claim 2 wherein said seeds are soaked in said solution for about 2–48 hours prior to planting.

4. The method of claim 1 wherein an aqueous solution having a concentration from about 0.0001–1.0 M of said N,N'-substituted urea is applied to said foliage at a rate of about 1–100 gm. of said substituted urea per acre.

5. The method of claim 4 wherein said solution further comprises a vegetable oil and a surfactant.

6. The method of claim 5 wherein said vegetable oil is selected from the group consisting of sunflower oil and soybean oil, and said surfactant is selected from the group consisting of organic polyphosphates and ethoxylated nonophenols.

7. A method for enhancing the growth of a plant, comprising applying to seeds for said plant prior to planting, to soil surrounding said plant or to foliage of said plant an N,N'-substituted urea selected from the group consisting of the reaction products formed by reacting a carboxylic acid having from 2 to 7 carbon atoms with urea where the molar ratio of carboxylic acid to urea is about 2:1.

8. The method of claim 7 wherein said carboxylic acid is acetic acid.

9. The method of claim 7 wherein said carboxylic acid has the formula RCOOH where R is selected from the group consisting of substituted and unsubstituted alkyl, allyl, vinyl and alkoxyl groups having from 1 to 6 carbon atoms, substituted and unsubstituted phenyl groups and the halides.

10. The method of claim 7 wherein said urea has the formula $(NHR^1)_2CO$ where each $R^1$ is the same or different and is selected from the group consisting of hydrogen, substituted and unsubstituted alkyl groups having from 1 to 6 carbon atoms, substituted and unsubstituted alkoxyl groups having from 1 to 6 carbon atoms, substituted and unsubstituted phenyl groups and the halides.

11. The method of claim 7 wherein an aqueous solution having a concentration from about 0.001–1.0 M of said N,N'-substituted urea is applied to said seeds at a rate of about 15–750 ml. of solution per 100 lbs. Of seed.

12. The method of claim 11 wherein said seeds are soaked in said solution for about 2–48 hours prior to planting.

13. The method of claim 7 wherein an aqueous solution having a concentration from about 0.0001–1.0 M of said N,N'-substituted urea is applied to said foliage at a rate of about 1–100 gm. of said substituted urea per acre.

14. The method of claim 13 wherein said solution further comprises a vegetable oil and a surfactant.

15. The method of claim 14 wherein said vegetable oil is selected from the group consisting of sunflower oil and soybean oil, and said surfactant is selected from the group consisting of organic polyphosphates and ethoxylated nonophenols.

16. The method of claim 9 wherein an aqueous solution having a concentration from about 0.001–1.0 M of said N,N'-substituted urea is applied to said seeds at a rate of about 15–750 ml. of solution per 100 lbs. of seed.

17. The method of claim 16 wherein said seeds are soaked in said solution for about 2–48 hours prior to planting.

18. The method of claim 9 wherein an aqueous solution having a concentration from about 0.0001–1.0 M of said N,N'-substituted urea is applied to said foliage at a rate of about 1–100 gm. of said substituted urea per acre.

19. The method of claim 18 wherein said solution further comprises a vegetable oil and a surfactant.

20. The method of claim 19 wherein said vegetable oil is selected from the group consisting of sunflower oil and soybean oil, and said surfactant is selected from the group consisting of organic polyphosphates and ethoxylated nonophenols.

* * * * *